United States Patent
Min et al.

(10) Patent No.: US 12,427,052 B2
(45) Date of Patent: Sep. 30, 2025

(54) METHOD FOR PRODUCING PATIENT-CUSTOMIZED PESSARY USING 3D PRINTER AND PATIENT-CUSTOMIZED PESSARY PRODUCED THEREBY

(71) Applicant: THE CATHOLIC UNIVERSITY OF KOREA INDUSTRY-ACADEMIC COOPERATION FOUNDATION, Seoul (KR)

(72) Inventors: Jae Young Min, Yongin-si (KR); Mee Ran Kim, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 323 days.

(21) Appl. No.: 18/020,818

(22) PCT Filed: May 17, 2021

(86) PCT No.: PCT/KR2021/006115
§ 371 (c)(1),
(2) Date: Feb. 10, 2023

(87) PCT Pub. No.: WO2022/145592
PCT Pub. Date: Jul. 7, 2022

(65) Prior Publication Data
US 2023/0285184 A1 Sep. 14, 2023

(30) Foreign Application Priority Data
Dec. 29, 2020 (KR) .................. 10-2020-0185945

(51) Int. Cl.
*A61F 6/08* (2006.01)
*B33Y 50/00* (2015.01)
*B33Y 80/00* (2015.01)

(52) U.S. Cl.
CPC ............. *A61F 6/08* (2013.01); *B33Y 50/00* (2014.12); *B33Y 80/00* (2014.12)

(58) Field of Classification Search
CPC ...... A61F 6/12; A61F 6/08; A61F 6/06; A61F 6/146; A61F 13/2068; A61F 13/15;
(Continued)

(56) References Cited

U.S. PATENT DOCUMENTS

| | | | |
|---|---|---|---|
| 2009/0266367 A1* | 10/2009 | Ziv | A61F 6/08 128/834 |
| 2019/0282350 A1* | 9/2019 | Conti | A61F 6/12 |
| 2022/0387158 A1* | 12/2022 | Sham | A61F 2/005 |

FOREIGN PATENT DOCUMENTS

| | | |
|---|---|---|
| JP | 2009-112830 A | 5/2009 |
| JP | 2014-509922 A | 4/2014 |

(Continued)

*Primary Examiner* — Ophelia A Hawthorne
(74) *Attorney, Agent, or Firm* — Bridgeway IP Law Group, PLLC; Jihun Kim

(57) ABSTRACT

Proposed are a method for producing a patient-customized pessary using a 3D printer and a patient-customized pessary produced thereby and, more specifically, a method for producing a patient-customized pessary using a 3D printer, for forming a pessary so as to correspond to the shape of a patient's vagina, and a patient-customized pessary produced thereby. The method for producing a patient-customized pessary using a 3D printer, comprises a) deriving the shape of a patient's vagina; b) 3D-modeling the shape of a pessary corresponding to the derived shape of the patient's vagina; and c) producing the pessary in the 3D-modeled shape by means of a 3D printer.

11 Claims, 7 Drawing Sheets

(58) Field of Classification Search
CPC ............... A61F 2/27; A61F 2250/0039; A61F 2250/0065; A61F 2250/01; A61F 6/18; A61B 17/42; A61M 2210/1433; A61K 9/0034; A61K 9/0036; A61L 15/16
See application file for complete search history.

(56) References Cited

FOREIGN PATENT DOCUMENTS

| | | | |
|---|---|---|---|
| JP | 2014-520896 | A | 8/2014 |
| KR | 10-1431051 | B1 | 8/2014 |
| KR | 10-2189639 | B1 | 12/2020 |
| WO | WO-2020181103 | A1 * | 9/2020 |

* cited by examiner

METHOD FOR PRODUCING PATIENT-CUSTOMIZED PESSARY USING 3D PRINTER AND PATIENT-CUSTOMIZED PESSARY PRODUCED THEREBY

TECHNICAL FIELD

The present invention relates to a method for producing a patient-customized pessary using a 3D printer and a patient-customized pessary produced thereby, and more particularly, to a method for producing a patient-customized pessary using a 3D printer for forming a pessary to correspond to a vaginal shape of a patient and a patient-customized pessary produced thereby.

BACKGROUND ART

Pelvic organ prolapse refers to a disease in which the abdominal organs protrude downward due to muscle weakness in the pelvic floor supporting the uterus, vagina, bladder, and rectum.

Such pelvic organ prolapse can be treated with exercise regimen and drug regimen in mild cases, but in severe cases, the sagging of the uterus must be fixed using surgical therapy or instruments.

In the treatment of patients with uterine prolapse, treatment using instruments such as a pessary is widely used, except for patients with very severe symptoms.

However, since conventional pessaries are not personalized, patients have to wear pessaries of various sizes in turn and try which size fits them, and if the size does not fit the patient, there is a problem that the pessary cannot be used.

In addition, the required pessary varies according to the shape of the vagina or the shape of the pelvis of the individual, but there is a problem that there is only one type of pessary currently available in Korea.

In addition, conventionally since the drug had to be directly administered by inserting a finger into the vagina, it was difficult to administer the drug regularly and there was a risk of inflammation.

DOCUMENTS OF RELATED ART

Japanese Laid-open Patent Publication No. 2014-509922

DISCLOSURE

Technical Problem

An object of the present invention to solve the above problems is to provide a method for producing a patient-customized pessary using a 3D printer for forming a pessary to correspond to a vaginal shape of a patient and a patient-customized pessary produced thereby.

The problems to be solved by the present invention are not limited to the problems mentioned above, and other problems not mentioned may be clearly understood by those skilled in the art from the following descriptions.

Technical Solution

In order to achieve the above objects, the configuration of the present invention provides a method for producing a patient-customized pessary using a 3D printer, including the steps of a) deriving a shape of a patient's vagina, b) 3D-modeling a shape of a pessary corresponding to the derived shape of the patient's vagina, and c) producing the pessary in the 3D-modeled shape by a 3D printer.

In an embodiment of the present invention, the step a) may include the steps of a1) inserting a balloon-shaped probe unit into the vagina; a2) injecting fluid into the probe unit inserted into the vagina to expand the probe unit; a3) measuring a pressure value for each position by a plurality of pressure sensors provided on an outer circumferential surface of the probe unit; and a4) deriving the shape of the patient's vagina using the pressure value for each position of the probe unit.

In an embodiment of the present invention, the step b) may be provided to model the shape of the pessary to correspond to the derived shape of the patient's vagina in the step a4).

In an embodiment of the present invention, the step a) may include the steps of i) inserting a balloon-shaped probe unit into the vagina; ii) injecting fluid into the probe unit inserted into the vagina to expand the probe unit; iii) deriving a shape of the probe unit by irradiating an ultrasonic wave on the probe unit; and iv) deriving the shape of the patient's vagina according to the shape of the probe unit.

In an embodiment of the present invention, the step b) may be provided to model the shape of the pessary to correspond to the derived shape of the patient's vagina in the step iv).

In an embodiment of the present invention, in the step b), the pessary may be modeled to inject any one or more of estrogen and lubricant.

In an embodiment of the present invention, in the step c), the 3D printer may be provided to print the pessary with a silicon material.

In an embodiment of the present invention, the step iv) may be provided to derive sagging of a uterus, rectum, and bladder according to the shape of the patient's vagina.

In an embodiment of the present invention, the step b) may be provided to model the shape of the pessary to support the uterus, rectum, and bladder in response to the derived sagging of the uterus, rectum, and bladder.

In order to achieve the above objects, the configuration of the present invention provides a patient-customized pessary using a 3D printer produced by the method for producing the patient-customized pessary using the 3D printer, including a pessary body provided to support a lower part of a uterus, wherein the pessary body is formed in a donut shape.

In an embodiment of the present invention, the pessary may further include a secretion hole formed in the pessary body; and a cylinder coupled to the pessary body and provided to store at least one of estrogen and lubricant, wherein at least one of the estrogen and the lubricant stored in the cylinder may be inserted through the secretion hole.

In an embodiment of the present invention, the pessary body may be provided to determine a thickness, aspect ratio, and maximum diameter of the donut shape in response to an amount of sagging of the uterus, rectum, and bladder.

Advantageous Effects

The effect of the present invention according to the configuration as described above is that it is possible to produce a pessary corresponding to a vaginal shape of a patient.

Drug regimen can be effectively performed by periodically secreting drugs from the secretion hole of the pessary.

The effect of the present invention is not limited to the above-mentioned effects, and it should be understood to include all possible effects deduced from the configuration of the invention described in the detailed description or the claims of the present invention.

BEST MODE FOR INVENTION

Figure 1:
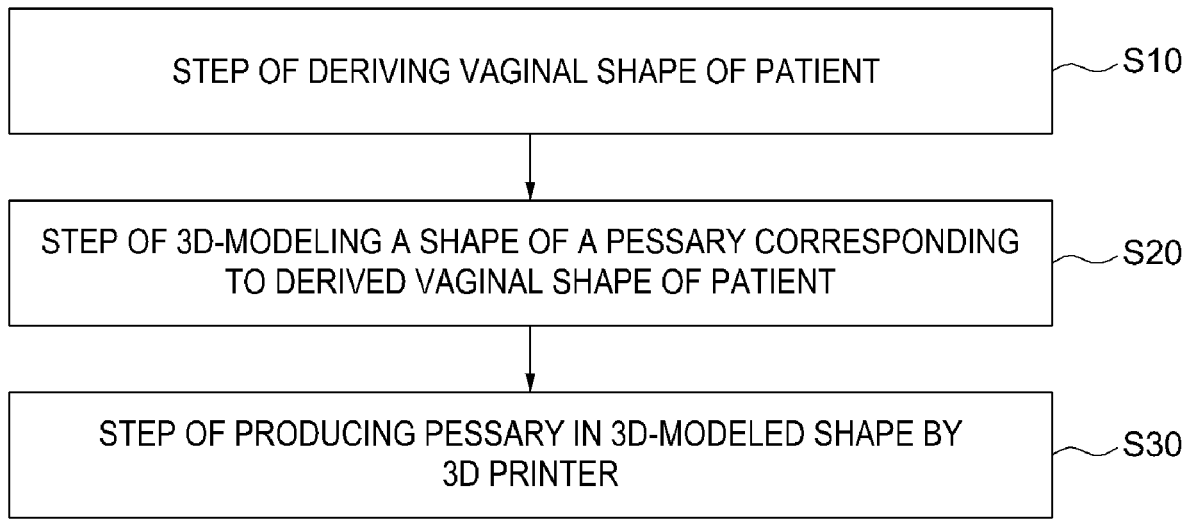
FIG. 1 is a flowchart of a method for producing a patient-customized pessary using a 3D printer according to an embodiment of the present invention.

A most preferred embodiment of the present invention is a method for producing a patient-customized pessary using a 3D printer, including the steps of deriving a shape of a patient's vagina; 3D-modeling a shape of a pessary corresponding to the derived shape of the patient's vagina; and producing the pessary in the 3D-modeled shape by a 3D printer. One of the most preferred embodiments according to the present invention, the step of deriving the shape of the patient's vagina; 3D modeling the shape of the pessary corresponding to the derived shape in the vagina of the patient; and manufacturing the pessary by a 3D printer in the 3D modeled shape.

MODE FOR INVENTION

Hereinafter, the present invention will be explained with reference to the accompanying drawings. The present invention, however, may be modified in various different ways, and should not be construed as limited to the embodiments set forth herein. Also, in order to clearly explain the present invention, portions that are not related to the present invention are omitted, and like reference numerals are used to refer to like elements throughout.

Throughout the specification, it will be understood that when an element is referred to as being "connected to (accessed, contacted, coupled,)" another element, it may be "directly connected to" the other element, or intervening elements or layers may be present. Also, it will also be understood that when a component "includes" an element, unless stated otherwise, it should be understood that the component does not exclude other elements but include further other elements.

The terminology used herein is for the purpose of describing various embodiments only and is not intended to be limiting. The singular forms are intended to include the plural forms as well, unless the context clearly indicates otherwise. It will be further understood that the terms "comprises," or "includes", when used herein, specify the presence of stated features, integers, steps, operations, elements, components or combination thereof, but do not preclude the presence or addition of one or more other features, integers, steps, operations, elements, components, or combinations thereof.

Hereinafter, embodiments of the present invention will be described in detail with reference to the accompanying drawings.

FIG. 1 is a flowchart of a method for producing a patient-customized pessary using a 3D printer according to an embodiment of the present invention.

Referring to FIG. 1, in the method for producing a patient-customized pessary using a 3D printer, first, the step (S10) of deriving a shape of a patient's vagina may be performed.

The step (S10) of deriving the shape of the patient's vagina may be provided to derive the shape of the vagina 1 of the patient.

Figure 2:
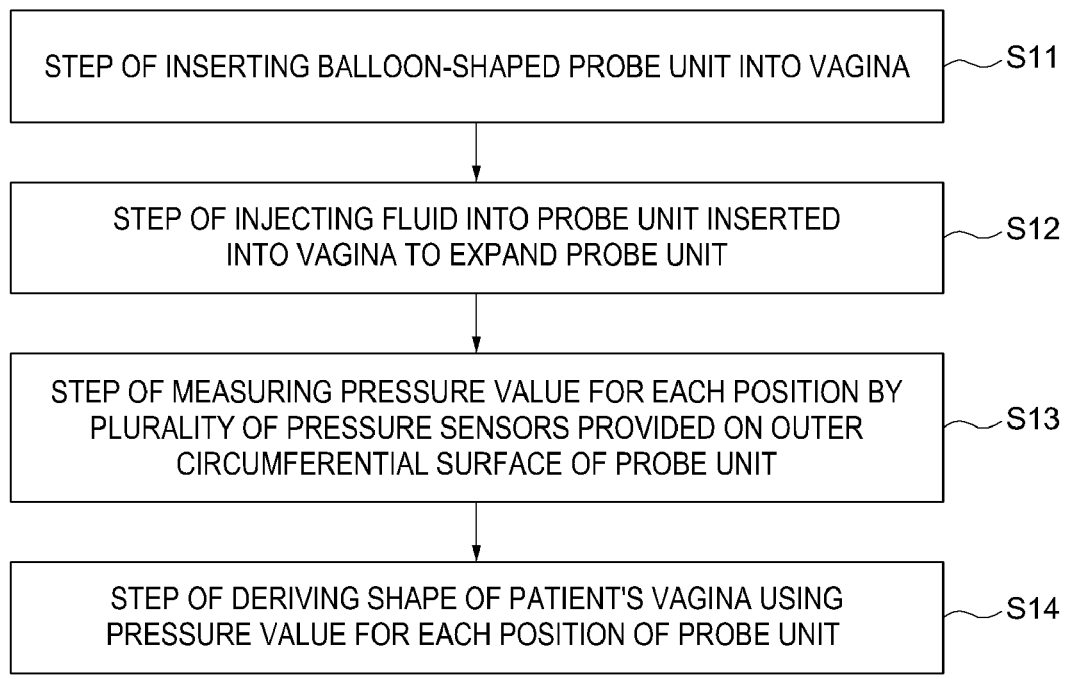
FIG. 2 is a flowchart of the step of deriving a shape of a patient's vagina according to a first embodiment of the present invention.
Figure 3:
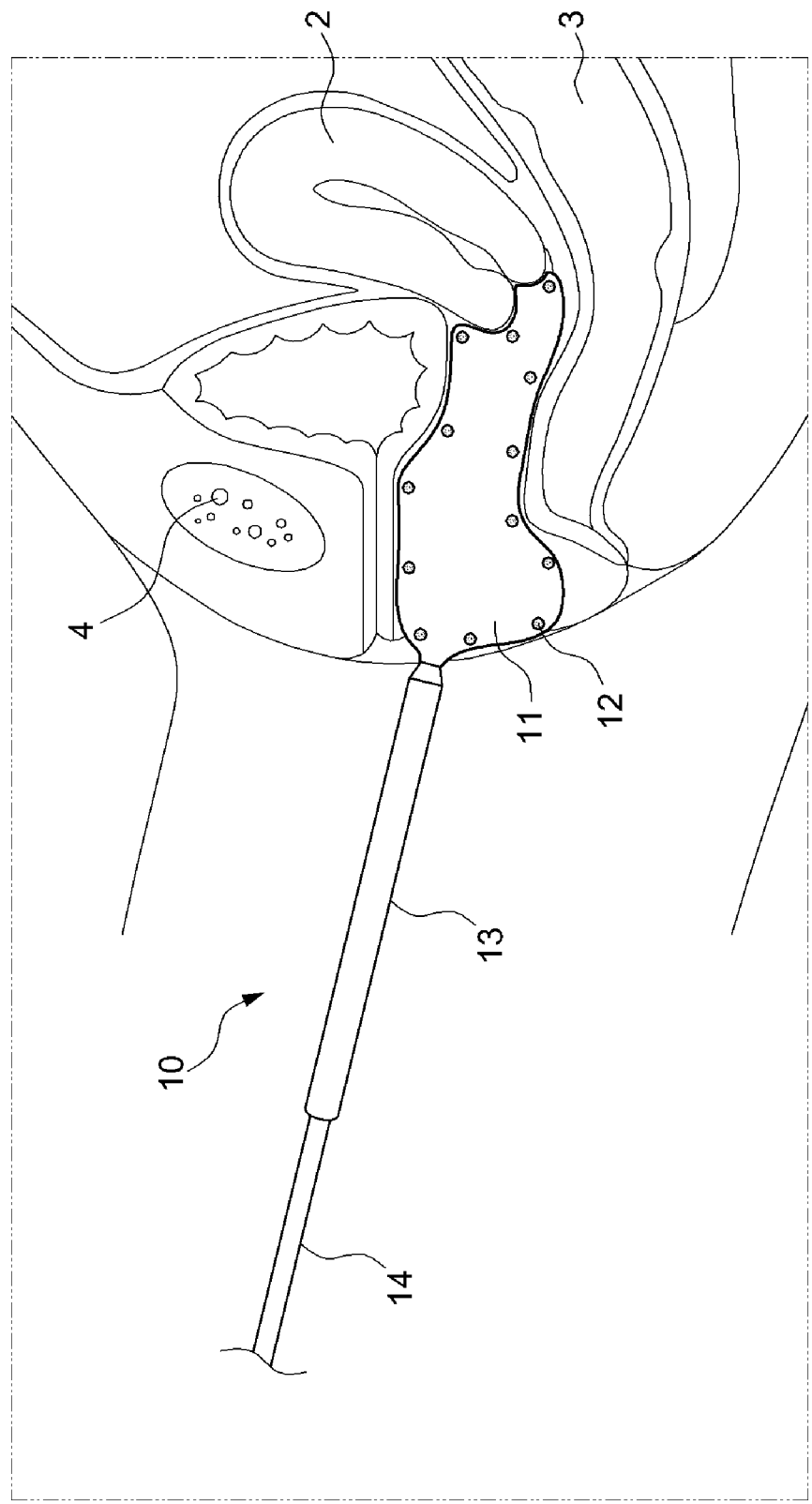
FIG. 3 is an exemplary view of a first probe unit according to an embodiment of the present invention.

FIG. 2 is a flowchart of the step of deriving a shape of a patient's vagina according to a first embodiment of the present invention, and FIG. 3 is an exemplary view of a first probe unit according to an embodiment of the present invention.

In the step (S10) of deriving the shape of the patient's vagina according to a first embodiment, the step (S11) of inserting a balloon-shaped probe unit into the vagina may be performed.

In the step (S11) of inserting the balloon-shaped probe unit into the vagina, the probe unit may be a first probe unit 10. The first probe unit 10 may include a balloon part 11, a pressure sensor 12, a handle 13, and an injection tube 14.

The balloon part 11 is formed to extend in a long direction and may be formed to be inserted into the vagina 1. Specifically, the balloon part 11 is formed to extend to have a length corresponding to the length of the vagina, and may be provided to be expandable as fluid is injected therein.

The pressure sensor 12 is formed on the outer circumferential surface of the balloon part 11 and may be provided in plurality. Specifically, the pressure sensor 12 may be formed at regular intervals along the circumference and longitudinal direction of the balloon part. In addition, the pressure sensor 12 may be provided to measure the pressure applied by the inner wall of the vagina 1 in response to the inflation of the balloon part 11.

The handle 13 may be formed to extend from the balloon part 11.

The injection tube 14 is formed to extend from the handle 13 and may be provided to inject fluid into the balloon part 11 or discharge fluid inside the balloon part 11.

In addition, a button connected to a valve may be provided on the handle 13 so that the injection tube 14 may control whether or not fluid is injected into the balloon part 11.

After the step (S11) of inserting the balloon-shaped probe unit into the vagina, the step (S12) of inserting fluid into the probe unit inserted into the vagina to expand the probe unit may be performed.

In the step (S12) of inserting fluid into the probe unit inserted into the vagina to expand the probe unit, fluid may be injected into the balloon part 11 using the injection tube 14. In response to the injection of fluid into the balloon part 11, the probe unit may be inflated and deformed into a shape corresponding to the shape of the vagina.

After the step (S12) of injecting fluid into the probe unit inserted into the vagina to expand the probe unit, the step (S13) of measuring a pressure value for each position by a plurality of pressure sensors provided on the outer circumferential surface of the probe unit may be performed.

In the step (S13) of measuring the pressure value for each position by a plurality of pressure sensors provided on the outer circumferential surface of the probe unit, the pressure sensor 12 may be provided to measure the pressure applied to the inner wall of the vagina 1 in response to inflation of the balloon part 11.

After the step (S13) of measuring the pressure value for each position by the plurality of pressure sensors provided on the outer circumferential surface of the probe unit, the step (S14) of deriving the shape of the patient's vagina using the pressure value for each position of the probe unit may be performed.

In the step (S14) of deriving the shape of the patient's vagina using the pressure value for each position of the probe unit, the first probe unit 10 may be provided to derive the internal shape of the vagina 1 according to the pressure value for each position measured by the pressure sensor 12. For example, as the inner space of the vagina 1 is wider, the pressure is relatively lowered, and as the inner space of the vagina 1 is narrower, the pressure is relatively increased. Using this, the internal shape of the vagina 1 may be derived according to the pressure value of each pressure sensor 12. Deriving the internal shape of the vagina 1 may be performed by a programming unit programmed to derive the internal shape of the vagina 1 through a change in a pressure value in real time.

In addition, in the step (S14) of deriving the internal shape of the patient's vagina using the pressure value for each position of the probe unit, a degree of derived due to the sagging of the uterus 2, rectum 3, and bladder 4 may be simultaneously measured through the shape of the vagina 1.

Figure 4:
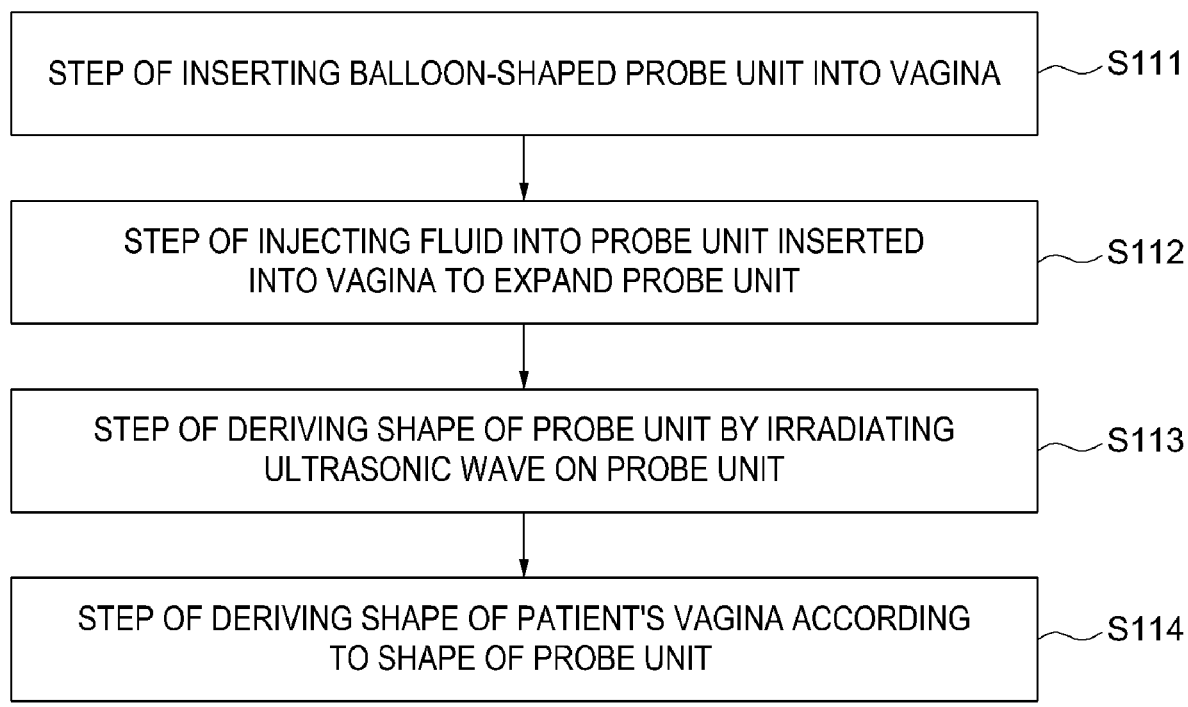
FIG. 4 is a flowchart of the step of deriving a shape of a patient's vagina according to a second embodiment of the present invention.
Figure 5:
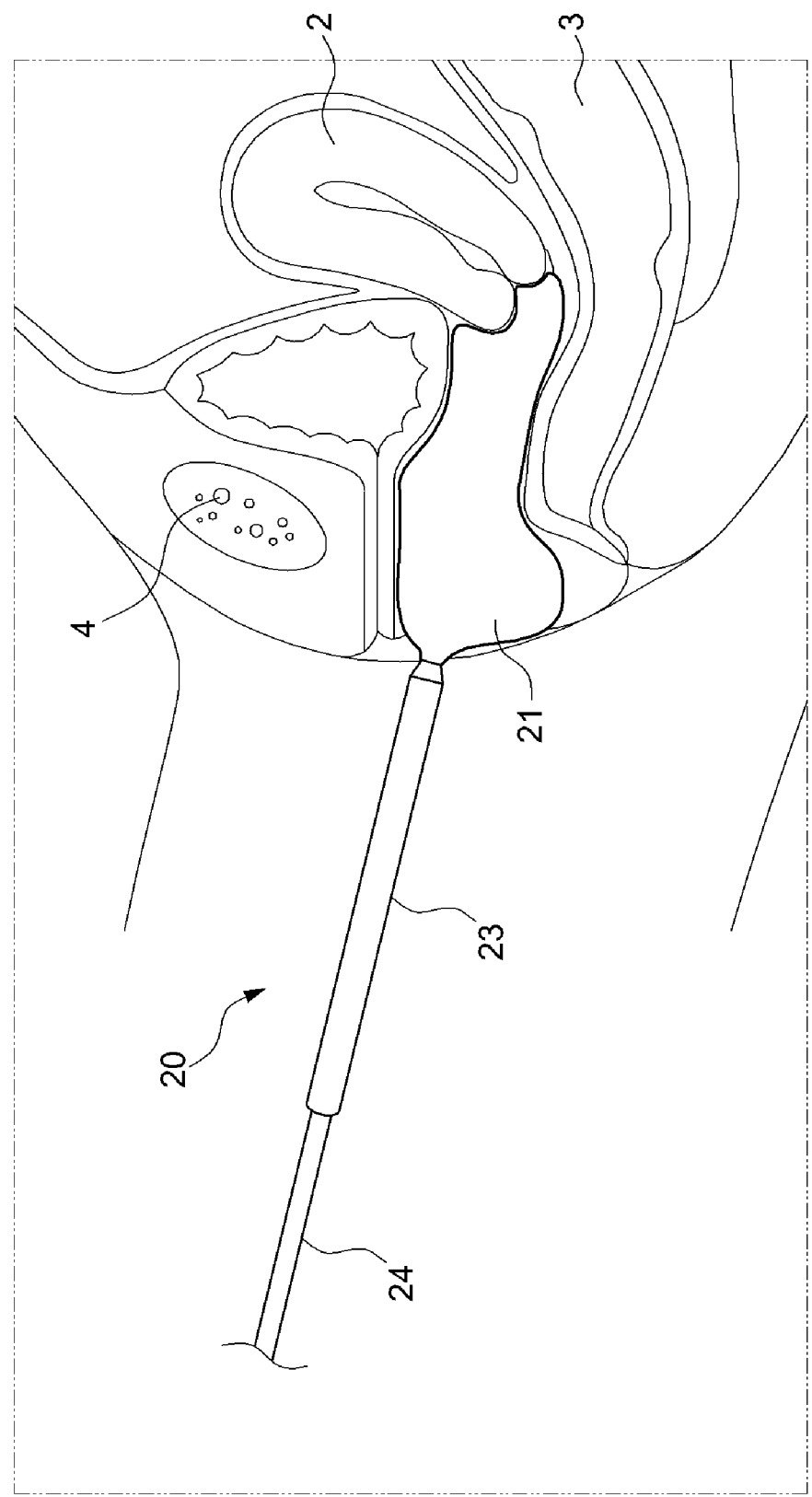
FIG. 5 is an exemplary view of a second probe unit according to an embodiment of the present invention.

FIG. 4 is a flowchart of the step of deriving a shape of a patient's vagina according to a second embodiment of the present invention, and FIG. 5 is an exemplary view of a second probe unit according to an embodiment of the present invention.

Referring to FIGS. 4 and 5, in the step (S10) of deriving the shape of the patient's vagina according to a second embodiment, first, the step (S111) of inserting a balloon-shaped probe unit into the vagina may be performed.

Here, the probe unit may be a second probe unit 20. The second probe unit 20 may include a balloon part 21, a handle 23, and an injection tube 24.

The balloon part 21 is formed to extend in a long direction and may be formed to be inserted into the vagina 1. Specifically, the balloon part 21 is formed to extend to have a length corresponding to the length of the vagina, and may be provided to be expandable as fluid is injected therein.

The handle 23 may be formed to extend from the balloon part 21.

The injection tube 24 is formed to extend from the handle 13 and may be provided to inject fluid into the balloon part 21 or to discharge fluid inside the balloon part 21.

In addition, a button connected to a valve may be provided on the handle 23 so that the injection tube 24 may be further provided to control whether or not fluid is injected into the balloon part 21.

After the step (S111) of inserting the balloon-shaped probe unit into the vagina, the step (S112) of inserting fluid into the probe unit inserted into the vagina to expand the probe unit may be performed.

In the step (S112) of inserting the fluid into the probe unit inserted into the vagina to expand the probe unit, the fluid may be injected into the balloon part 21 using the injection tube 24. In response to the injection of fluid into the balloon part 21, the balloon part may be expanded and deformed into a shape corresponding to the shape of the vagina.

After the step (S112) of injecting the fluid into the probe unit to expand the probe unit, the step (S113) of deriving the shape of the probe unit by irradiating ultrasonic waves on the probe unit may be performed.

In the step (S113) of deriving the shape of the probe unit by irradiating the ultrasonic waves on the probe unit, an ultrasound unit may be provided to irradiate ultrasonic waves on the second probe unit 20. In response to the irradiation of ultrasonic waves on the second probe unit 20, the shape of the second probe unit 20 may be captured by the fluid inside the second probe unit 20.

In the step (S113) of deriving the shape of the probe unit by irradiating ultrasonic waves on the probe unit, in order to more accurately derive the shape of the second probe unit 20, the ultrasonic waves may be irradiated in various directions to photograph the shape of the second probe unit 20 at various angles.

After the step (S113) of deriving the shape of the probe unit by irradiating the ultrasonic waves on the probe unit, the step (S114) of deriving the shape of the patient's vagina according to the shape of the probe unit may be performed.

The step (S114) of deriving the shape of the patient's vagina according to the shape of the probe unit may be provided to derive the shape of the vagina 1 using the shape of the second probe unit 20.

For example, the shape of the vagina 1 may be derived by combining shapes of the balloon part 21 of the second probe unit 20 photographed from various angles.

As such, the present invention may be provided to accurately derive the shape of the patient's vagina using the first probe unit 10 or the second probe unit 20.

In addition, the step (S114) of deriving the shape of the patient's vagina according to the shape of the probe unit may be provided to simultaneously measure a degree of derived due to the sagging of the uterus 2, rectum 3, and bladder 4 through the shape of the vagina 1.

After the step (S10) of deriving the shape of the patient's vagina, the step (S20) of 3D modeling the shape of the pessary corresponding to the derived shape of the patient's vagina may be performed.

The step (S20) of 3D modeling the shape of the pessary corresponding to the derived shape of the patient's vagina may be provided to model a shape of the pessary suitable for the above derived shape of the patient's vagina.

Figure 6:
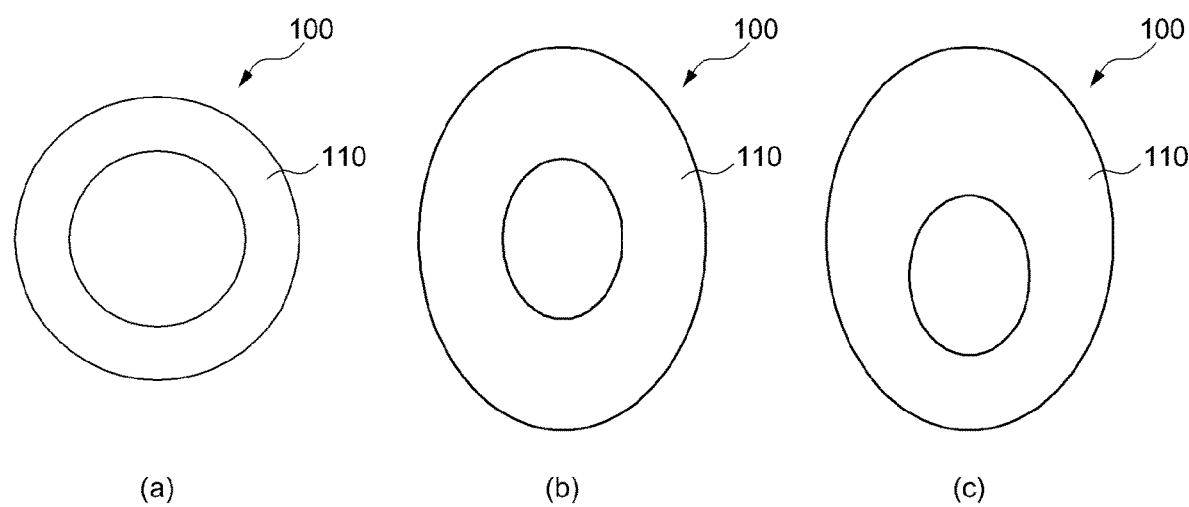
FIG. 6 is an exemplary view of a pessary according to a first embodiment of the present invention.
Figure 7:
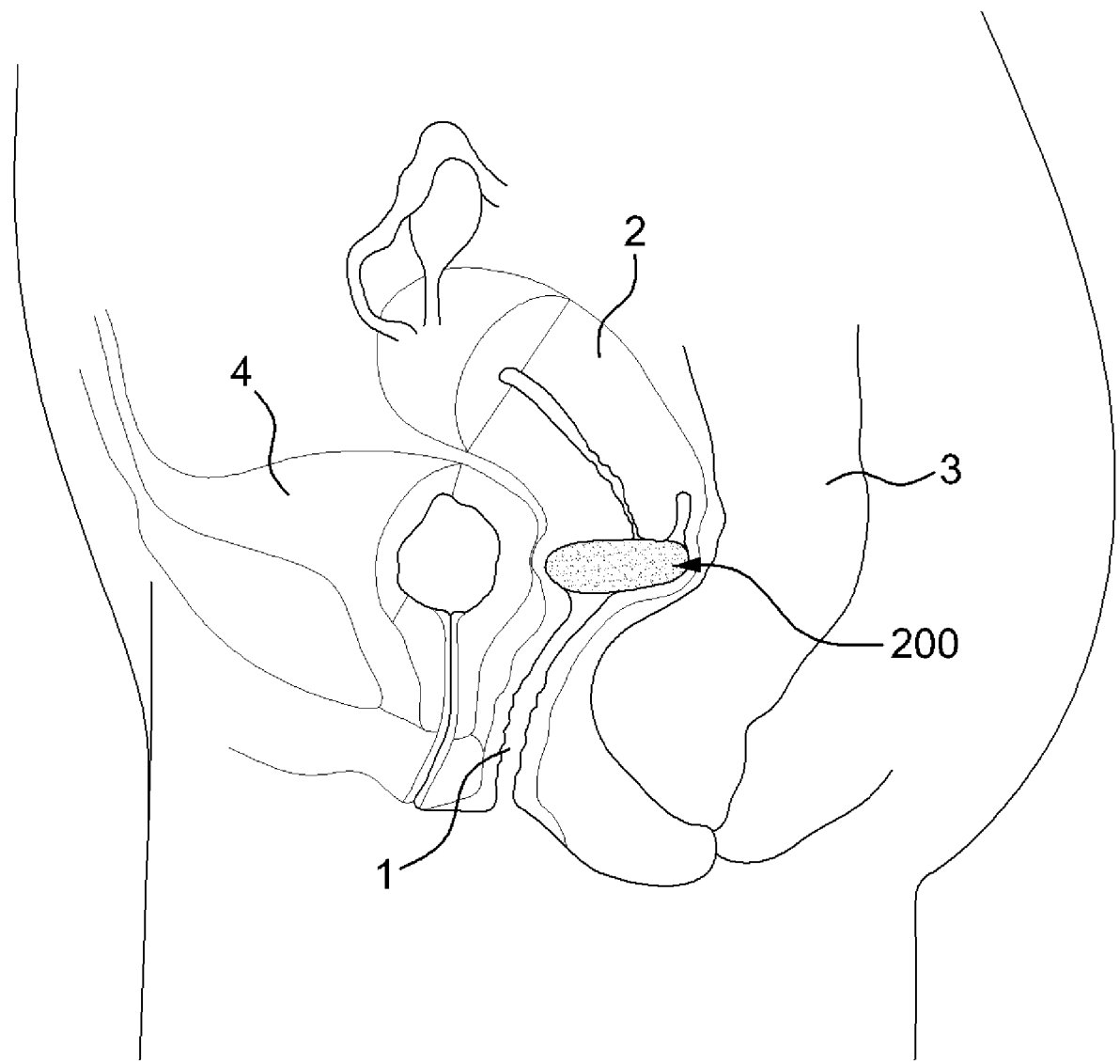
FIG. 7 is an exemplary view showing a state in which a pessary according to a first embodiment of the present invention is seated on a vagina.

FIG. 6 is an exemplary view of a pessary according to a first embodiment of the present invention, and FIG. 7 is an exemplary view showing a state in which a pessary according to a first embodiment of the present invention is seated on a vagina.

Referring to FIGS. 6 and 7, in the step (S10) of deriving the shape of the patient's vagina, if the uterus 2 of the patient is protruding downward, the pessary 100 may be provided in the lower part of the uterus 2 to support the uterus 2.

Specifically, the pessary 100 according to the first embodiment may include a pessary body 110 that is formed in a donut shape and is inserted into the vagina 1 below the uterus 2 to prevent the uterus 2 from descending downward.

In addition, in the step (S20) of 3D modeling the shape of the pessary corresponding to the derived shape of the patient's vagina, the shape of the pessary may be modeled to support the uterus 2, rectum 3, and bladder 4 in response to the degree of derived due to the sagging of the uterus 2, rectum 3, and bladder 4 derived according to the derived vagina 1.

To this end, the pessary body 110 may be provided to determine the thickness, aspect ratio, and maximum diameter of the donut shape in response to the degree of sagging of the uterus, rectum, and bladder.

For example, in the case that it is necessary to support only the sagging of the uterus 2, the pessary body 110 may be formed into a donut shape having the same aspect ratio as shown in (a) of FIG. 6. However, in the case that the sagging occurs in the rectum 3 and the bladder 4 in addition to the uterus 2, the pessary body 110, as shown in (b) of FIG. 6, may be extended with changed thickness and aspect ratio to support the sagged rectum 3 and bladder 4.

As another example, in the case that the sagging occurs in any one of the rectum 3 and the bladder 4 in addition to the uterus 2, as shown in (c) of FIG. 6, the pessary body 110 may be provided so that the aspect ratio is modified and extended so that the thickness of the pessary body 110 becomes thicker toward the sagging organ in order to support the sagging organ.

As such, according to the present invention, the shape of the pessary 100 may be modified to support the sagging of not only the uterus 2 but also the rectum 3 and the bladder 4.

Figure 8:
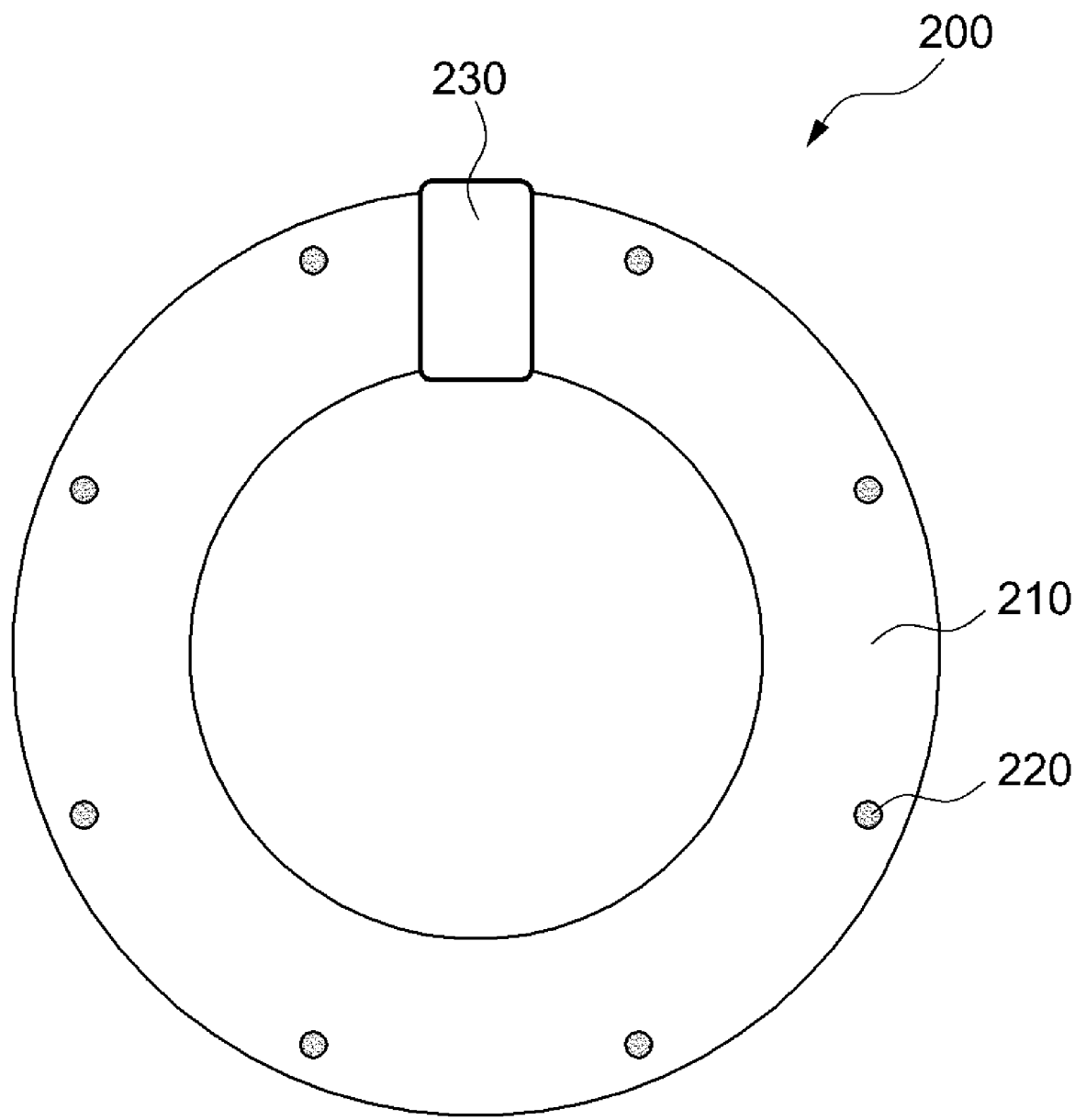
FIG. 8 is an exemplary view of a pessary according to a second embodiment of the present invention.

FIG. 8 is an exemplary view of a pessary according to a second embodiment of the present invention.

Referring to FIG. 8, in the step (S10) of deriving the shape of the patient's vagina, the pessary 200 according to the second embodiment may include a pessary body 210 that is formed in a donut shape and inserted into the vagina 1 at the lower part of the uterus 2 to prevent the uterus 2 from descending downward.

In addition, the pessary 200 may further include a secretion hole 220 formed in the pessary body 210 and a cylinder 230 coupled to the pessary body 210 to store at least one of estrogen and lubricant.

One or more of the secretion hole 220 may be provided in a circumferential direction of the pessary body 210, and may be provided to periodically discharge any one or more of estrogen and lubricant.

That is, in the step (S10) of deriving the shape of the patient's vagina, the vaginal shape and the degree of sagging of the uterus 2, rectum 3, and bladder 4 may be determined, and depending on the degree of sagging of the uterus 2, it may be determined whether the patient needs hormone treatment such as estrogen or lubricant treatment.

In this way, in the step (S20) of 3D modeling the shape of the pessary corresponding to the shape of the patient's vagina, in the case of the existence of derivation due to the sagging of the rectum (3) and bladder (4) other than the uterus (2), as well as the shape of the vagina 1, and the need for lubrication or hormonal treatment such as estrogen, the pessary may be modeled such that the secretion hole 220 and the cylinder 230 are formed in the pessary body 210. Such pessary modeling may be performed by a modeling unit.

In this case, the cylinder 230 may be provided to set a time interval and secretion amount of lubrication or estrogen through the secretion hole 220. Due to this, it is possible to improve the treatment effect by continuously injecting an appropriate amount of drug required by the patient at a predetermined time.

After the step (S20) of 3D modeling the shape of the pessary corresponding to the derived shape of the patient's vagina, the step (S30) of producing the pessary by a 3D printer in the 3D modeled shape may be performed.

In the step (S30) of producing the pessary by a 3D printer in a 3D modeled shape, the pessary may be formed by 3D printing in the form previously modeled by the modeling unit.

In this case, the 3D printing may be made of a harmless silicone material even if the material is inserted into the human body.

On the other hand, the pessary of the present invention may be also provided with a shape memory alloy material. Specifically, like the shape memory alloy principle in which a size changes at a specific temperature, the pessary of the present invention may be made to increase in size only up to a certain pressure in the vagina, so that the size is automatically adjusted according to the size of the internal space of the vagina 1.

According to the present invention provided as described above, the sagging of the uterus 2, rectum 3, and bladder 4 can be simultaneously measured by measuring the shape of the vagina 1 of the patient. Through this, it is possible to produce and use the pessary modeled in an optimized form according to the patient. That is, according to the present invention, the pessary can be stably inserted into the vagina and maintained in a fixed state, and can support organs such as the uterus 2 as well as the rectum 3 and bladder 4 to prevent sagging of the organs.

In addition, according to the present invention, since the drug is secreted periodically, the possibility of inflammation is less than when the drug is directly injected, and the drug can be injected without missing, so that the treatment effect can be improved.

The above description of the present invention is provided for the purpose of illustration, and it would be understood by those skilled in the art that various changes and modifications may be made without changing technical conception and essential features of the example embodiments. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present invention is defined by the following claims, and it shall be understood that all modifications and embodiments conceived from the meaning and scope of the claims and their equivalents are included in the scope of the present invention.

DESCRIPTION OF REFERENCE NUMERALS

1: vagina
2: uterus
3: rectum
4: bladder
10: first probe unit
11: balloon part
12: pressure sensor
13: handle
14: injection tube
20: second probe unit
21: balloon part
23: handle
24: injection tube
100: pessary
110: pessary body
120: secretion hole
200: pessary
210: pessary body
220: secretion hole
230: cylinder

The invention claimed is:

1. A method for producing a patient-customized pessary using a 3D printer, the method comprising:
    deriving a shape of a vagina;
    3D-modeling a shape of a pessary corresponding to the shape of the vagina; and
    producing the pessary in the 3D-modeled shape of the pessary by a 3D printer,
    wherein the deriving of the shape of the vagina includes:
    inserting a balloon-shaped probe unit into the vagina;
    injecting fluid into the balloon-shaped probe unit inserted into the vagina to expand the balloon-shaped probe unit;
    measuring a pressure value for each position of the balloon-shaped probe unit by a plurality of pressure sensors provided on an outer circumferential surface of a balloon part of the balloon-shaped probe unit; and
    deriving the shape of the vagina using the pressure value for each position of the balloon-shaped probe unit,
    wherein the plurality of pressure sensors are disposed on the outer circumferential surface of the balloon part of the balloon-shaped probe unit at regular intervals to contact an inner wall of the vagina and an outer wall of a cervix in response to inflation of the balloon part, such that the plurality of pressure sensors are capable of measuring a pressure applied at a recess between the inner wall of the vagina and the outer wall of the cervix.

2. The method of claim 1, wherein the deriving of the shape of the vagina further includes:
    deriving a shape of the balloon-shaped probe unit by irradiating an ultrasonic wave on the balloon-shaped probe unit; and
    deriving the shape of the vagina according to the shape of the balloon-shaped probe unit.

3. The method of claim 2, wherein the deriving of the shape of the vagina according to the shape of the balloon-shaped probe unit is performed to derive sagging of a uterus, rectum, and bladder according to the shape of the vagina.

4. The method of claim 3, wherein the 3D-modeling is performed to model the shape of the pessary to support the uterus, rectum, and bladder in response to the derived sagging of the uterus, rectum, and bladder.

5. The method of claim 2, wherein the 3D-modeling is performed to model the shape of the pessary corresponding to the shape of the vagina derived according to the shape of the balloon-shaped probe unit derived by irradiating the ultrasonic wave on the balloon-shaped probe unit.

6. A patient-customized pessary printer produced by the method for producing the patient-customized pessary using the 3D printer of claim 1, the patient-customized pessary comprising:
    a pessary body configured to support a lower part of a uterus,
    wherein the pessary body has a donut shape.

7. The patient-customized pessary of claim 6, further comprising:
    a secretion hole defined in the pessary body; and
    a cylinder coupled to the pessary body and configured to store at least one of estrogen and lubricant,
    wherein the secretion hole is configured to secrete therethrough the at least one of the estrogen and the lubricant stored in the cylinder.

8. The patient-customized pessary of claim 6,
    wherein the pessary body has a thickness, aspect ratio, and maximum diameter of the donut shape determined to correspond to an amount of sagging of the uterus, rectum, and bladder.

9. The method of claim 1, wherein the 3D-modeling is performed to model the shape of the pessary corresponding to the shape of the vagina derived using the pressure value for each position of the balloon-shaped probe unit.

10. The method of claim 1, wherein in the 3D-modeling, the pessary is modeled to secrete at least one of estrogen and lubricant.

11. The method of claim 1, wherein in the producing of the pessary in the 3D-modeled shape by a 3D printer, the 3D printer is provided to print the pessary with a silicon material.

* * * * *